(12) United States Patent
Kania et al.

(10) Patent No.: US 7,157,614 B1
(45) Date of Patent: Jan. 2, 2007

(54) TREATMENT DEVICES PROVIDING TARGETED ANTIMICROBIAL ACTION

(75) Inventors: Bruce G. Kania, Bozeman, MT (US);
Robert O. Becker, Lowville, NY (US);
John Scofield, Clarks Summit, PA (US)

(73) Assignee: Fountainhead, LLC, Shepherd, MT (US)

(*) Notice: Subject to any disclaimer, the term of this patent is extended or adjusted under 35 U.S.C. 154(b) by 654 days.

(21) Appl. No.: 10/027,394

(22) Filed: Dec. 21, 2001

Related U.S. Application Data

(60) Provisional application No. 60/257,520, filed on Dec. 21, 2000.

(51) Int. Cl.
*A61F 13/00* (2006.01)

(52) U.S. Cl. .................. 602/41; 602/48; 424/443

(58) Field of Classification Search ............ 602/41–59; 128/888, 889; 424/443–449
See application file for complete search history.

(56) References Cited

U.S. PATENT DOCUMENTS

| | | | |
|---|---|---|---|
| 2,934,066 A | 4/1960 | Stowasser |
| 3,092,552 A | 6/1963 | Romans |
| 3,249,109 A | 5/1966 | Maeth et al. |
| 3,800,792 A | 4/1974 | McKnight et al. |
| 3,830,908 A | 8/1974 | Klippel et al. |
| 3,903,882 A | 9/1975 | Augurt |
| 4,142,521 A | 3/1979 | Konikoff |
| 4,376,763 A | 3/1983 | Barth et al. |
| 4,460,369 A | 7/1984 | Seymour |
| 4,525,410 A | 6/1985 | Hagiwara et al. |
| 4,603,152 A | 7/1986 | Laurin et al. |
| 4,638,796 A | 1/1987 | Sims |
| 4,657,006 A | 4/1987 | Rawlings et al. |
| 4,703,108 A | 10/1987 | Silver et al. |
| 4,728,323 A | 3/1988 | Matson |
| 4,753,231 A | 6/1988 | Lang et al. |
| 4,767,401 A | 8/1988 | Seiderman |
| 4,808,402 A | 2/1989 | Leibovich et al. |
| 4,817,594 A | 4/1989 | Juhasz |
| 4,860,737 A | 8/1989 | Lang et al. |
| 4,906,466 A | 3/1990 | Edwards et al. |
| 4,911,688 A | 3/1990 | Jones |
| 4,933,178 A | 6/1990 | Capelli |
| 4,938,955 A | 7/1990 | Niira et al. |
| 4,938,958 A | 7/1990 | Niira et al. |
| 5,094,847 A | 3/1992 | Yazaki et al. |
| 5,180,585 A | 1/1993 | Jacobson et al. |
| 5,210,882 A | 5/1993 | Moretz et al. |
| 5,217,782 A | 6/1993 | Moretz et al. |
| 5,218,973 A | 6/1993 | Weaver et al. |
| 5,297,296 A | 3/1994 | Moretz et al. |
| 5,326,567 A | 7/1994 | Capelli |

(Continued)

OTHER PUBLICATIONS

Spadaro, J. A., et al., "Antibacterial Effects of Silver Electrodes with Weak Direct Current," *Antimicrobial Agents & Chemotherap.*, vol. 6, No. 5 (1974), pp. 637-642.

(Continued)

*Primary Examiner*—Henry Bennett
*Assistant Examiner*—Annette Dixon

(57) ABSTRACT

A treatment device having an antimicrobial sheet material operably connected to an appliance. The antimicrobial material includes a first layer of polymeric material such as a gel composition containing a block copolymer and mineral oil, and a second layer that contains a bactericidal metal such as silver. The appliance retains the antimicrobial material in a selected position in the user's mouth, nose, or other body cavity; it may assume a variety of configurations depending on position and extent of the treatment site.

11 Claims, 5 Drawing Sheets

U.S. PATENT DOCUMENTS

| | | |
|---|---|---|
| 5,340,363 A | 8/1994 | Fabo |
| 5,395,398 A | 3/1995 | Rogozinski |
| 5,413,789 A | 5/1995 | Hagiwara et al. |
| 5,423,874 A | 6/1995 | D'Alerta |
| 5,478,563 A | 12/1995 | Erami |
| 5,603,122 A | 2/1997 | Kania |
| 5,681,645 A | 10/1997 | Strack et al. |
| 5,782,788 A | 7/1998 | Widemire |
| 5,814,094 A | 9/1998 | Becker et al. |
| 5,856,245 A | 1/1999 | Caldwell et al. |
| 5,939,339 A | 8/1999 | Delmore et al. |
| 5,958,440 A | 9/1999 | Burrell et al. |
| 6,017,553 A | 1/2000 | Burrell et al. |
| 6,087,549 A * | 7/2000 | Flick .......................... 602/41 |

OTHER PUBLICATIONS

Berger, T. J., "Antifungal Properties of Electrically-Generated Metallic Ions," Antimicrobial Agents & Chemotherapy, vol. 20, No. 5 (1976), pp. 856-860.

Becker, R. O., et al., "Treatment of Orthopaedic Infections With Electrically-Generated Silver Ions" *J. Bone & Joint Surgery*, vol. 60-A, No. 7 (1978), pp. 871-881.

* cited by examiner

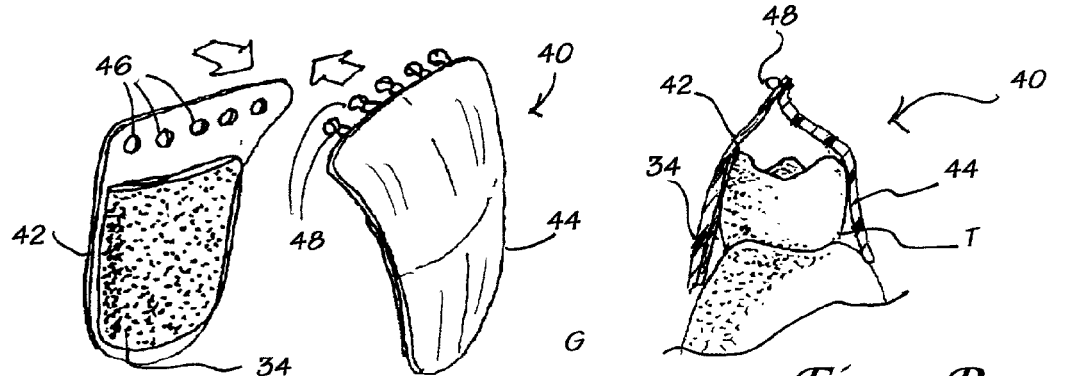
*Fig. 3A*
*Fig. 3B*
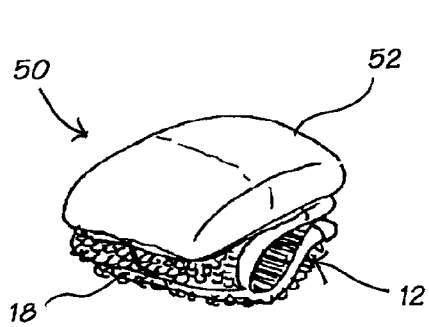
*Fig. 4A*
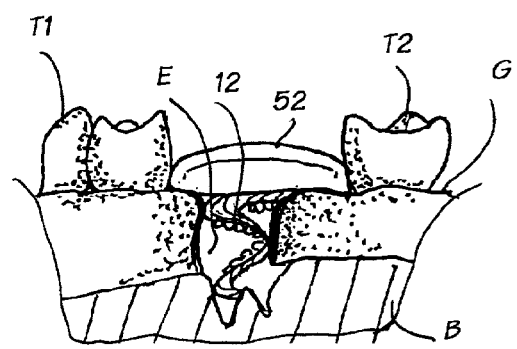
*Fig. 4B*
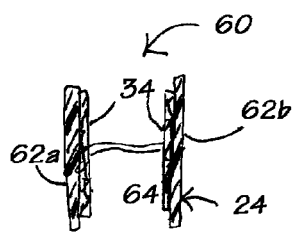
*Fig. 5A*
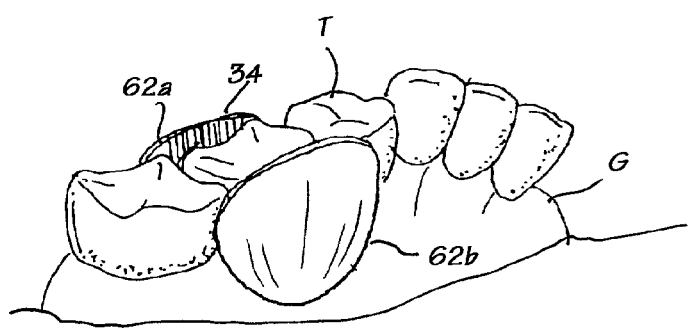
*Fig. 5B*

TREATMENT DEVICES PROVIDING TARGETED ANTIMICROBIAL ACTION

This application claims the benefit of U.S. Provisional Application(s) No(s).: APPLICATION No(S).: 60/257,520 FILING DATE Dec. 21, 2000.

BACKGROUND OF THE INVENTION

1. Field of the Invention

The present invention relates to antimicrobial treatment devices. In particular, the present invention relates to treatment devices that make use of the antimicrobial properties of silver to provide targeted, localized antimicrobial action for dental, periodontal and other treatment purposes.

2. Discussion of Background

The care and treatment of wounds is an important part of health care, incorporating the sometimes-irreconcilable goals of satisfactory outcomes, responsiveness to patient concerns, and cost-effectiveness. Wound healing is a cellular process which is triggered by the occurrence of an injury (as used herein, the terms "wound" and "injury" refer to tissue damage or loss of any kind, including but not limited to infections, cuts, incisions (including surgical incisions), abrasions, lacerations, fractures, contusions, burns, amputations, and so forth). Healing is believed to be controlled by a biophysiological feedback mechanism that monitors the extent of the injury and controls cellular activity in the injured area to produce the types and numbers of cells needed to accomplish a repair.

Many conditions can impact normal healing processes, including impaired circulation, conditions such as diabetes, and infections at the situs of the injury which frequently result in non-healing or slowly-healing wounds, unfavorable outcomes, and increased health care costs. In response to these concerns, many hospitals have established specialized centers to treat non-healing wounds. A wide variety of treatment modalities, including local and systemic antibiotics, antibiotic-impregnated dressings, antibiotic and antifungal compositions, and the like are available for treating infected wounds, slowly-healing wounds, and non-healing wounds. Many of these are used prophylactically in an attempt to forestall infections, which are a growing concern due to the spread of antibiotic-resistant strains of bacteria.

Periodontal disease in particular can be difficult to treat due to these and other factors such as diet, non-optimum dental hygiene (which permits the accumulation of minute food particles in the junction area between the tooth and the gum tissue), lack of dental care (due to lack of access to care and/or reluctance to seek care when needed), localized infections, and systemic conditions. Since the advent of fluoride treatment and the resulting decrease in cavities, periodontal disease has become the single greatest cause of tooth loss in the adult population of the U.S. and other developed countries. It is estimated that over half the adult population of the U.S. has some degree of periodontal disease.

Periodontal disease is characterized by the recession of gum tissue from the bases of the involved teeth in a process which exposes dentine tissue and produces "pockets" of infection that extend along the roots of the teeth. If unchecked, this process eventually results in loosening of the roots in the bone sockets and ultimately loss of the affected teeth. The pathogenesis of periodontal disease is believed to be infection with a variety of bacteria, beginning at the gum line with the formation of plaque (a biofilm consisting of bacteria encased in a mucopolysaccharide material secreted by the bacteria) which acts as an irritant to the underlying tissues. If the plaque is not removed periodically (as by routine cleaning by a trained dental hygienist), this condition becomes chronic and eventually extends into the space formed by the junction between the soft tissue of the gum and the tooth root. The infection results in edema (swelling) and irritation of the gum tissues, further enhancing the infection and permitting its extension into the space between the tooth root and the gum, and ultimately between the tooth and the bone socket.

Presently-available treatments for periodontal disease include the removal of plaque, surgical removal of the infected gum tissue (in a procedure commonly termed "scaling") and rigorous local treatment (including brushing, flossing, antiseptic mouth washes, and antibiotics). Because local administration of antibiotics frequently produces local tissue sensitivity reactions which worsen the condition, systemic antibiotics are preferred. Disadvantages of antibiotic treatment include the known side effects of many antibiotics, the potential for the development of antibiotic-resistant strains of bacteria, and the resulting need for frequent changes in the antibiotics administered to any particular patient. Such modalities require extended, expensive treatment with frequent patient monitoring. Even after successful treatment, recurrence is common unless the patient follows a rigorous program of dental hygiene and diet (low-carbohydrate diets are sometimes helpful in preventing periodontal disease). Thus, there is a need for alternative treatments to address the growing problem of periodontal disease. Treatment approaches that permit targeted delivery of antibiotics to the affected areas would alleviate the problems associated with the use of systemic antibiotics, and also help those patients who find it difficult or impossible to maintain a rigorous program of dental hygiene.

Silver and other metals are widely used in antimicrobial and antifungal applications, including topical preparations (creams, ointments, etc.) as well as wound dressings. (For purposes of this specification, an "antimicrobial metal" is one with "antibiotic," "antimicrobial," "cidal," "bactericidal" and/or "bacteristatic" properties, broadly defined as a metal that is active against at least one pathogenic microorganism, including but not limited to bacteria, protozoa, fungi, rickettsiae, and viruses. Bactericidal agents kill microorganisms, whereas bacteristatic agents prevent their growth and multiplication.). Silver has good bioactivity against a broad spectrum of microorganisms, at relatively low concentrations, thus, it is perhaps the most widely-used antimicrobial metal. Topical preparations that contain silver or silver compounds—silver nitrate, silver sulfadiazine, colloidal silver compositions, silver-protein compounds such as Argyrol™, and so forth—are widely used in medicine. For example, ointments containing silver sulfadiazine are widely used for the treatment of infected burns.

The effectiveness of silver as an antimicrobial agent is at least partly determined by the delivery system. Most silver compounds that dissociate readily yield cations that are highly toxic to human tissues, and therefore are not considered suitable for medical use. Less-toxic compounds, including silver sulfadiazine cream (widely used in the treatment of burns) and silver nitrate solution, do not dissociate readily. These topical compounds must therefore be re-applied frequently to maintain their clinical efficacy.

Iontophoretic (i.e., electrically-generated) silver ions, which can penetrate more deeply into the tissues than silver ions from topical compounds, have been found to inhibit bacterial and fungal growth in vivo and in vitro at current densities as low as 10 nA/mm$^2$. Silver ions are effective even against antibiotic-resistant strains of bacteria and fungi. Iontophoretic silver treatment is somewhat more effective than treatment with silver compounds, with generally the same spectrum of activity as that of silver nylon. The effects of electrically-generated silver ions are described in a number of publications, including the following: J. A. Spadaro, et al., "Antibacterial Effects of Silver Electrodes with Weak Direct Current," *Antimicrobial Agents & Chemotherapy*, Vol. 6, pp. 637–642 (1974); T. J. Berger, et al., "Antifungal Properties of Electrically Generated Metallic Ions," *Antimicrobial Agents & Chemotherapy*, Vol. 10, pp. 856–860 (1976); R. O. Becker, et al., "Treatment of Orthopedic Infections With Electrically-Generated Silver Ions," *J. Bone & Joint Surgery*, Vol. 60-A, pp. 871–881 (1978)), incorporated herein by reference.

Silver and other metals are used in a number of wound dressings, in the form of pure metal, metal salts, or other compounds. Wound dressings that contain silver or silver compounds are described by McKnight, et al. (U.S. Pat. No. 3,800,792), Weaver, et al. (U.S. Pat. No. 5,218,973), Fabo (U.S. Pat. No. 5,340,363), Klippel, et al. (U.S. Pat. No. 3,830,908), Stowasser (U.S. Pat. No. 2,934,066), and Matson (U.S. Pat. No. 4,728,323). Dressings and devices for the administration of electrical stimulation include those described by Konikoff (U.S. Pat. No. 4,142,521), Rogozinski (U.S. Pat. No. 5,395,398), Silver, et al. (U.S. Pat. No. 4,703,108), D'Alerta (U.S. Pat. No. 5,423,874), Jones (U.S. Pat. No. 4,911,688), Juhasz (U.S. Pat. No. 4,817,594), Seiderman (U.S. Pat. No. 4,767,401), Becker, et al. (U.S. Pat. No. 5,814,094, incorporated herein by reference), and Flick (U.S. Pat. No. 6,087,549).

Many different materials are used for manufacturing wound dressings, surgical gowns and masks, surgical drapes, and like products. Available materials may include flexible, conformable substrates, moisture-absorbing layers, gas-permeable and liquid-impermeable layers, selectively-permeable layers, non-adhering or self-adhering layers, and moisture-absorbing layers, of natural fibers or man-made compositions. Antibacterial agents may be added for therapeutic purposes or to increase the shelf life of the product.

By way of example, Kania (U.S. Pat. No. 5,603,122, incorporated herein by reference) describes a form-fitting sleeve member that incorporates a polymeric cushioning material (most preferably a thermoplastic elastomer, silicon-containing elastomer, or thermoset silicone). Delmore, et al. (U.S. Pat. No. 5,939,339) discloses a bandage having a porous, self-adhering elastic substrate which does not adhere to clothing, hair or skin, and which has a permanent compressive force that is sufficient to hold it in place. Caldwell, et al. (U.S. Pat. No. 5,856,245) describe a polymer composition that is impermeable to liquids, permeable to gases, and impermeable (or selectively permeable) to microorganisms. The fabric can incorporate a wide range of additives including growth factor, wound healing proteins such as collagen, electromagnetic and electrostatic shielding agents, electrically conducting agents, and a variety of antimicrobial agents.

Additional materials are described by Strack, et al. (U.S. Pat. No. 5,681,545), Moretz, et al. (U.S. Pat. Nos. 5,217,782; 5,210,882; 5,297,296), Hagiwara, et al. (U.S. Pat. No. 4,525, 410), Seymour (U.S. Pat. Nos. 4,460,369 and 4,340,043). Wound dressings are disclosed by Widemire (U.S. Pat. No. 5,782,788), Lang, et al. (U.S. Pat. Nos. 4,860,737 and 4,753,231), Matson (U.S. Pat. No. 4,728,323), Rawlings, et al. (U.S. Pat. No. 4,657,006), Augurt (U.S. Pat. No. 3,903, 882), McKnight, et al. (U.S. Pat. No. 3,800,792), Maeth, et al. (U.S. Pat. No. 3,249,109), and Stowasser, et al. (U.S. Pat. No. 2,934,066). Sims (U.S. Pat. No. 4,638,796) provides a method for dressing a wound with a nonadherent, nonabsorbent, conformable material, followed by an absorbent dressing. An antimicrobial agent may be applied to the material.

Wound dressings and other products may include antimicrobial additives to retard spoilage and increase product shelf life. See, for example, Erami (U.S. No. 5,478,563), Hagiwara, et al. (U.S. Pat. No. 5,413,789), Niira, et al. (U.S. Nos. U.S. Pat. Nos. 4,938,958 and 4,938,955), and Barth, et al. (U.S. Pat. No. 4,376,763). Some products contain leachable antimicrobial compositions, for example, Capelli (U.S. Pat. Nos. 5,326,567 and 4,933,178), Jacobson, et al. (U.S. Pat. No. 5,180,585), Yazaki, et al. (U.S. Pat. No. 5,094,847), Edwards, et al. (U.S. Pat. No. 4,906,466), Leibovich, et al. (U.S. Pat. No. 4,808,402), Laurin, et al. (U.S. Pat. No. 4,603,152), and Romans (U.S. Pat. No. 3,092,552).

Our application Ser. No. 09/431,991, filed Nov. 3, 1999 ("Multilayer Antimicrobial Treatment Device"); the disclosure of which is incorporated herein by reference, describes a multilayer device having at least one layer of a silver-containing fabric that that is effective against sepsis-causing and odor-causing microorganisms, at least one moisture-absorbing layer, and, optionally, an outer, moisture-impermeable and gas-permeable layer that serves as an occlusive barrier for directing fluids to the silver-containing layer. The silver is attached to the fabric in a mechanically stable form that releases ionic silver when wetted. The material can be used for prophylactic and therapeutic care and treatment of skin infections and surface wounds (including surgical incisions), as a wound packing material, and as an adjuvant to conventional deodorants. The device is made of nontoxic, nonhazardous, nonallergenic materials, and is inert until activated by contact with perspiration or other suitable liquid.

Application Ser. No. 60/183,599, filed Feb. 18, 2000 and Ser. No. 60/197,010, filed Apr. 13, 2000, the disclosures of which are incorporated herein by reference, disclose a multilayered antimicrobial composition in sheet form, and articles of manufacture that include the composition. The composition includes a layer of polymeric material and a layer containing an antibacterial metal; in a preferred embodiment, the polymeric material is a gel composition comprising a block copolymer and, optionally, mineral oil; the antibacterial layer is provided by coating the gel composition with silver, incorporating silver into the gel composition, or attaching a silver-containing fabric to the gel composition. The composition itself is durable, nontoxic, nonhazardous, substantially nonallergenic and nonirritating, and inert until activated by contact with a suitable liquid (water, perspiration, wound exudate, hydrocolloid, etc.).

Despite the availability of a variety of wound dressings, antimicrobial compositions, delivery systems (both passive and iontophoretic) for supplying bactericidal metals such as silver to a treatment site, there is a need for simple, versatile, cost-effective devices that provide targeted antimicrobial action for dental (including periodontal), post-surgical, and other applications.

SUMMARY OF THE INVENTION

According to its major aspects and broadly stated, the present invention is a treatment device including an antimicrobial sheet material operably connected to an appliance. The antimicrobial sheet material includes a bactericidal metal such as silver; preferably, the antimicrobial sheet material has a first layer of polymeric material and at least one second layer that contains the bactericidal metal. The appliance retains the antimicrobial sheet material in a selected position in the user's mouth (or other treatment site); it may assume any of a variety of configurations depending on location and extent of the treatment site. The device may be used for treatment of periodontal disease and other oral conditions, extraction sites, and surgical incisions.

The antimicrobial sheet material is a major feature of the present invention, being at least somewhat flexible and conformable so that it can be shaped into configurations useful for the invention. The first layer of the antimicrobial material is preferably a polymeric gel composition that includes a gel or combination of gels, foamed or non-foamed, with a durometer hardness that somewhat approximates that of human skin. Other suitable materials include block copolymers with, optionally, mineral oil, thermoplastic materials, and indeed any natural or synthetic materials with the requisite properties.

The second layer of the antimicrobial sheet material contains silver, which is effective against a broad spectrum of microorganisms including but not limited to sepsis-causing bacteria and odor-causing bacteria. The silver is preferably in a mechanically stable form that remains bound to the composition when dry, but that rapidly begins to release useful amounts of silver ions on a sustainable basis when moistened by a liquid such as water, saline solution, hydrocolloid solution, wound exudate, saliva, perspiration, and so forth. Thus, when the second layer contacts the target area in the patient's mouth (or other treatment site), at least a portion of the silver contained therein is released into the surrounding tissues with resulting beneficial effects. The antimicrobial second layer itself is durable, nontoxic, nonhazardous, substantially nonallergenic and nonirritating, and inert until activated by contact with a suitable liquid (water, saline solution, hydrocolloid solution, wound exudate, saliva, perspiration, etc.). While silver is preferred, other metals, alloys, or compounds of these metals or alloys may also be useful.

The appliance is an important feature of the present invention. The appliance can be of virtually any size and shape that is operable to retain the antimicrobial sheet material in a selected position engaging the area to be treated. For example, the appliance may be a brace, splint, or perio-chip that carries a suitable amount of the antimicrobial sheet material. Alternatively, the appliance may be a cap, bite block, bite plate, or other device that retains the antimicrobial sheet material in an extraction site or in contact with an affected tooth. The appliance forms a substrate that may be adapted for treating one tooth and/or the surrounding gum, a plurality of teeth, the entire upper or lower jaw, the nasal cavity, or other body cavities, as will be described in the following Detailed Description.

Other features and advantages of the present invention will be apparent to those skilled in the art from a carefull reading of the Detailed Description of Preferred Embodiments presented below and accompanied by the drawings.

BRIEF DESCRIPTION OF THE DRAWINGS

FIGS. 3A and 3B are perspective and cross-sectional views of still another treatment device according to the invention;

FIGS. 4A and 4B are perspective and partial cross-sectional views, respectively, of a dental packing device according to the present invention;

FIGS. 5A and 5B are side and perspective views, respectively, of yet another treatment device according to the invention;

DETAILED DESCRIPTION OF PREFERRED EMBODIMENTS

Figure 1A:
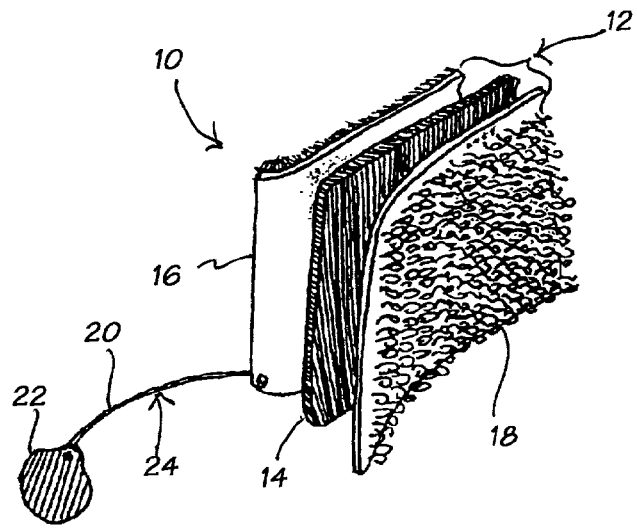
FIGS. 1A and 1B are a partially-exploded perspective view and a side view, respectively, of a periodontal treatment device according to a preferred embodiment of the present invention.

In the following detailed description of the invention, reference numerals are used to identify structural elements, portions of elements, surfaces or areas in the drawings, as such elements, portions, surfaces or areas may be further described or explained by the entire written specification. For consistency, whenever the same numeral is used in different drawings, it indicates the same element, portion, surface or area as when first used. Unless otherwise indicated, the drawings are intended to be read together with the specification, and are to be considered a portion of the entire written description of this invention as required by 35 U.S.C. § 112.

A preliminary study was undertaken with volunteer patients. Silver-containing fabric was used for targeted delivery of an antimicrobial metal (silver), demonstrating the effectiveness of localized treatment for periodontal disease. In the study, silver-containing nylon fabric was cut into strips measuring approximately 1 cm wide by 6–8 cm long. The strips were moistened with tap water, and positioned appropriately for 1–2 hours, twice daily. Three volunteer patients were treated, as described further below.

Example 1

A 75-year-old female presented with severe periodontal disease including pockets of 6 mm depth and several loose teeth. Recommended conventional treatment included scaling and systemic antibiotics.

Strips of silver-containing nylon fabric were prepared as described above and placed between the patient's lip and gum so as to cover the affected area. The fabric was kept in place for 1–2 hours, twice daily.

Within a few days of starting treatment with the silver-containing fabric, swelling and redness of the gingival tissue decreased, accompanied with a decrease in reported patient discomfort. After approximately 1–2 weeks of treatment, the affected areas exhibited no redness and swelling, although the presence of gum recession, pockets, and loosened teeth persisted. Approximately one month after start of treatment, the affected gums appeared more normal, with clinically obvious regrowth of gum tissue and diminution of pocket depth. Tightening of loose teeth was noted between 1 and 2 months following start of treatment; regrowth of gum papillae (i.e., those portions of the gums which extend between neighboring teeth) was evident within 5–6 months. As the appearance of the treated gums improved, treatment was decreased to once per day, then to once every other day until the gums appeared normal.

After completion of treatment, the patient was instructed to continue with a maintenance schedule of twice weekly treatments (i.e., once every 3–4 days) to prevent a recurrence of periodontal disease. Without such prophylactic treatment, the condition would likely recur due to the persisting causative factors of diet, plaque buildup, and the retention of food particles between the teeth in the average patient.

Example 2

A 76-year-old male had simultaneous extractions of two adjacent lower incisors under standard local anesthesia, leaving a single, large socket defect. Immediately following the extractions (while the socket was bleeding freely), pre-cut strips of silver nylon fabric (3 mm×2 cm) were packed into the socket by the dental surgeon. A large bite block covered with a single layer of silver nylon fabric was applied. As the anesthesia wore off, the patient reported that there was no pain in the treated area.

The bite block was removed at 2 hours post extraction, and the patient's mouth was gently irrigated while leaving the packing intact. The silver nylon packing was removed at 4 hours post extraction and a second bite block was applied. The second block was removed at 6 hours post extraction, at which time there was no pain, swelling or redness in the area.

At 12 hours post extraction; a double layer of silver nylon fabric was laid over the entire area and retained in position for approximately 2 hours. There was no treatment overnight; the patient did not require analgesics. The following day (day 2), granulation tissue was evident in the socket; there was no pain, swelling or redness. Treatment with silver nylon fabric was done twice, for 2 hours each time. By day 3, the socket had virtually healed; a single treatment with silver nylon fabric was done in the evening. By day 4, the treated area was essentially normal and the gum was fully healed, with no pain swelling, or redness.

Example 3

A 33-year-old male underwent a difficult extraction of an impacted right second molar. This patient was treated identically to Example 2, with the exception that the extraction socket was not packed until approximately ½ hour post extraction. The patient had been administered an analgesic due to the difficulty in extraction. The course was essentially the same as for Example 2; the patient did not require further analgesics.

While the above-described treatment regimen was surprisingly effective in treating periodontal disease and extraction sites, the use of silver-containing fabric alone has some practical difficulties that preclude its widespread use for treatment of periodontal disease. The wet fabric lacks dimensional stability, and furthermore tends to migrate out of position resulting in inconsistent treatment.

Referring now to the Figures, there are shown treatment devices each having a portion of antimicrobial sheet material in combination with a dental or periodontal appliance that permits secure positioning in a patient's mouth during use to provide targeted antimicrobial action. Treatment devices according to the present invention include devices for treating single teeth, a group of two or more neighboring teeth, selected gum tissue, and the entire upper or lower jaw, as may be needed for a particular patient's condition. The invention also includes devices for treating soft tissues in or near the oral and nasal cavities.

Figure 1B:
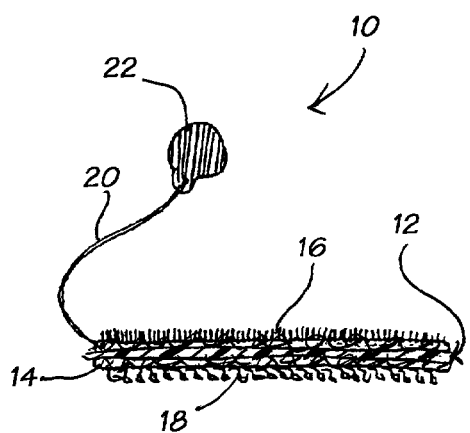

FIGS. 1A and 1B show a treatment device 10 according to a preferred embodiment of the present invention (the shading in these and the following Figures is intended solely to assist the viewer in distinguishing the various components of the devices shown therein). Device 10 includes a multilayer antimicrobial sheet 12 having layers 14, 16, and 18 (to be described further below), and a tether 20 and a disk 22 that together form an appliance 24. Tether 20 is preferably a thin, flexible monofilament nylon fiber affixed at one end to sheet 12 and at the other end to disk 22. Alternatively, tether 20 may made of virtually any biocompatible, substantially nonallergenic, natural or synthetic fiber, for example, the types of fiber used for products such as dental floss.

Disk 22 is made of some biocompatible plastic with an approved dermal adhesive (such as SKIN BOND) applied to one surface thereof. The adhesive is covered with a peel-off plastic or paper disc which is removed prior to use. Disk 22 is attached to tether 20 by a biocompatible adhesive, crimping, application of heat and/or pressure, or other suitable technique. Tether 20 and/or disk 22 may be transparent or translucent, and may be tinted in any selected color (for example, to coordinate with human skin tones).

Sheet 12 is an antimicrobial sheet material having antimicrobial properties as defined above, preferably marked in some way so that the user can readily distinguish the outer surface of layer 18 from the other side of the sheet. Suitable markers include tags or other suitable means known in the art. Alternatively, one of the visible layers of sheet 12 is colored so that the user can readily distinguish it from the other layers. Sheet 12 includes an inner layer 14 of polymer material, an optional support layer 16, and at least one layer 18 that contains silver or other suitable antimicrobial metal. Layer 14 may comprise a polymeric gel composition, for example, the composition described in our pending application 60/183,599 and Ser. No. 60/197,010 (the disclosures of these applications are incorporated herein by reference).

While silver-containing layer 18 may be added by coating layer 12 with silver or incorporating silver therein, layer 18 preferably consists of a silver-containing fabric such as silver nylon material attached to polymer layer 14. While silver is preferred, other metals and compounds with useful antimicrobial properties may also be useful. Suitable fabrics for layer 18 include silver-impregnated brush tricot fabric, smooth surface tricot fabric, knit loop fabric, pile fabric, and other fabrics that contain useful amounts of silver, made of nylon or other suitable fibers. (The optimum fabric for any particular application is best determined by a modest amount of observation and experimentation.) Such fabrics are made by Omnishield, Inc., Swift, Inc., Sauquoit Industries, and other manufacturers. The most preferred fabric for layer 18 is a loop knot fabric or a pile fabric that is applied to layer 14 such that the rough (i.e., loop or pile) side is exposed. This structure (shown in FIG. 1A) permits a close approximation of layer 18 to the irregularities of the teeth and gums (or other tissues being treated) and also maximizes the available surface area for emission of silver ions. Silver may be added to the fabric by any suitable technique. Indeed, the metal content of layer 18 as well as the thickness, structure, and uniformity of the metal coating, may vary broadly depending on the intended application. However, it should be understood that the material for layer 18 is selected with a view to providing the needed amounts of free silver to the treatment site. Other metals that exhibit antibacterial and/or antifungal properties may also be useful for the practice of the present invention, including but not limited to gold, copper, platinum, aluminum, zinc, titanium, and combinations and alloys thereof.

The silver in layer 18 is preferably in a form that, when device 10 is placed in contact with body tissues and moistened by a suitable liquid, the device releases silver ions by the passive dissolution of silver in an ionic form from the metallic silver surface in a process known as oligodynamic action. Over a period of time, at least a portion of the available silver migrates to the immediately-adjacent tissues where it has useful antimicrobial and antifungal effects.

While not wishing to be bound by theory, it is believed that metallized (i.e., metal-containing, metal-coated, metal-plated) materials wherein the metal atoms are firmly attached or bound to a fabric substrate when dry, but are at least somewhat releasable in ionic form when wetted with a suitable liquid, are especially suitable for the practice of the present invention. For example, layer 18 may contain silver in the form of small hexagonal, tabular crystals, deposited throughout the fabric, which tend to release free silver ions when wetted by saline, water, saliva, wound exudate, or other suitable liquid. Crystalline silver deposits of this type are believed to have a greater effective surface area than conventional silver-plated coatings, and therefore the capability of releasing more silver ions per unit coating weight, in shorter periods of time.

The rate and extent of silver release from layer 18 is at least partly determined by the nature of the silver deposits on the fabric substrate. For fabrics that contain crystalline silver as described above, the rate of silver efflux from the fabric reaches a maximum during the first few minutes after immersion in distilled water. The maximum rate from 30 g of fabric (containing 21 wt. % silver) was 0.7 PPM, decreasing to a plateau of approximately 3.7 PPM after 72 hours immersion. Considerably higher plateau levels (over 50 PPM) were measured in physiological media such as Eagle's MEM biological culture medium.

Other types of silver-containing materials may also be useful for layer 18, where the silver (or other antimicrobial metal) is be in the form of a powder, flakes, foil, coating, or other useful form. For example, antimicrobial metals in powder form may be deposited onto a substrate, forming a coating with sufficient atomic disorder that the resulting material releases atoms, ions, molecules, or clusters containing silver on a sustained basis when in contact with an alcohol or a water based electrolyte (see, for example, U.S. Pat. No. 5,958,440 and U.S. Pat. No. 6,017,553). This type of coating, and other useful types of coatings, may be formed on layer 16, or directly on one or both surfaces of layer 12. A discussion of suitable silver-containing fabrics is included in our co-pending applications as listed above, which are incorporated herein by reference.

Layer 16 provides additional dimensional stability and position retention to device 10. Layer 16, if present, may consist of plain (i.e., not silvered, not metallized) nylon or other fabric. For example, layer 16 may be a brushed tricot nylon material, attached to layer 14 so that the brushed surface of the nylon fabric is facing outwards as shown in FIG. 1A. When constructed in this manner, the brushed, textured outer surfaces of sheet 12 assist in retaining device 10 in position in the user's mouth.

Layer 16 may also be a somewhat malleable (i.e., shapeable, formable) material that the user (or a medical or dental practitioner) can readily conform so as to engage the treatment site. In this embodiment, the material of layer 16 is substantially inert, nonirritating and nonallergenic. In addition, the material is one that, once formed into a particular shape, tends to retain that shape until it is re-shaped by the user. Alternatively, layer 16 may be a flexible material that incorporates shapeable rails (made of wire or other shape-holding material).

Layers 16 and 18 may be attached to layer 14 by any convenient technique, including but not limited to heat/pressure bonding, crimping, embossing, sonic welding, needle punching and biocompatible adhesives. Alternatively, hook-and-loop or groove-and-rib type closures may be useful (these types of closures are described in co-pending application Ser. No. 09/431,991, filed Nov. 3, 1999, and Ser. No. 09/496,766, filed Feb. 3, 2000, the disclosures of which are incorporated herein by reference). The materials of layers 14, 16, 18 are soft, flexible, compressible, and well tolerated by virtually all patients.

Device 10 is used for dental or periodontal treatment where targeted delivery of the antimicrobial agents in layer 18 is desired. For example, device 10 may be inserted into the patient's mouth and positioned appropriately for carrying out the desired treatment (for example, between the gum and the lip or cheek), with tether 20 exiting the mouth at a corner of the lips. A small area of the skin near the vermilion border of the lips is cleaned with alcohol. Disk 22 is placed on the cleaned skin and secured in place by the adhesive.

Device 10 may also be used to treat conditions in the user's nasal cavity and other body cavities, and for treating lacerations, infections, surgical incisions, wounds, scrapes, and so forth where targeted, localized antimicrobial activity is needed. The device can be provided in any size, shape, or configuration; thus, it can readily be adapted for a variety of applications.

While device 10 is in place, layer 18 releases silver ions which have been demonstrated to be effective against a variety of bacteria (including antibiotic-resistant strains, Gram-positive strains, and Gram-negative strains). Tether 24 helps retain device 10 in place while the patient goes about his normal activities (however, tether 24 may be removed if preferred by the individual patient). At the end of the prescribed treatment time, the patient simply removes and discards device 10. The action of normally-occurring skin oils may be sufficient to loosen disk 22 within a few hours; however, solvents may be used to loosen the adhesive on disk 22 if needed.

Device 10 may be used for treatment of dental or periodontal conditions, including but not limited to treatment of periodontal disease and treatment of extraction sites. Device 10 (and other devices to be described below) may also be used for treatment of soft tissue conditions, injuries, and surgical incisions in the oral, nasal, and other body cavities. For example, device 10 may be useful in treating conditions such as genital herpes, and herpes simplex (commonly known as "cold sores" or "canker sores") in or near the patient's mouth or nose.

Figure 2A:
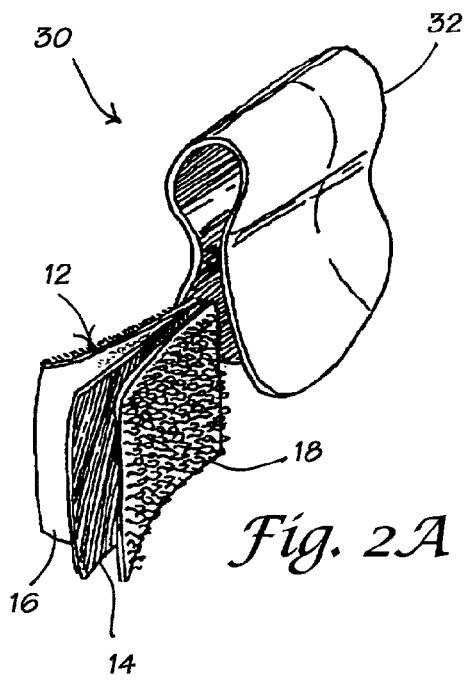
FIGS. 2A–C show another treatment device according to the present invention.
Figure 2B:
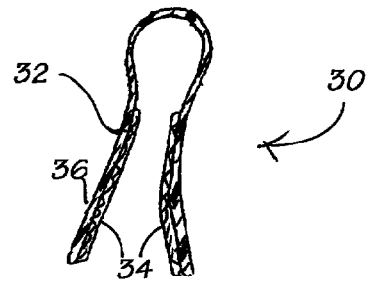
Figure 2C:
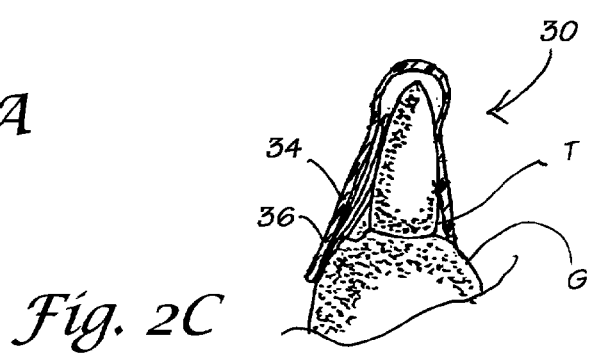

Sheet 12 may be combined with other suitable appliances and tethering devices, resulting in a variety of treatment devices for dental, periodontal, and other applications. For example, FIGS. 2A–C show a dental or periodontal treatment device 30 where appliance 24 consists of a brace 32 of roughly "clothes-pin" configuration. Brace 32 may be made of a somewhat flexible, resilient, plastic material that is substantially inert, nonirritating and nonallergenic. More preferably, the material may be somewhat malleable, that is, once formed into a particular shape, the material tends to retain that shape until it is re-shaped by the user.

At least one liner 34 made of an antimicrobial sheet material (such as sheet 12) is attached to an inner surface of brace 32 with a dental adhesive (FIG. 2B). When device 30 is placed over a patient's tooth T as shown in FIG. 2C, the skirt portion 36 of brace 32 extends down over the gum G. Thus, liner 34 contacts the tooth and gum surfaces to be treated to provide localized, targeted antimicrobial action as described above for device 10. The provision of two liners 34 permits treatment of both sides of the gum simultaneously.

FIGS. 3A and 3B show still another periodontal treatment device 40 having an appliance 24 made up of two sections 42, 44. The sections 42, 44 snap together via holes 46 and pins 48, respectively. One or both of sections 42, 44 has a liner 34 of sheet 12 attached thereto, by a biocompatible adhesive or other suitable means. Sections 42, 44, like above-described brace 32, are made of a somewhat flexible, somewhat resilient plastic material. In use, sections 42 and 44 form a brace around a tooth T (for clarity, tooth T and gum G are shown in cross-section in FIG. 3B).

FIGS. 4A and 4B illustrate a dental packing device 50 according to the invention, wherein a dental appliance 50 includes sheet 12 used with a "cap" or "bite block" 52 that is configured for placement over an empty socket E following a tooth extraction. At least one strip of fairly thick material 12 is packed into the socket and covered by bite block 52; two or more such strips may be used where needed.

When positioned for treatment, bite block 52 substantially fills the gap between the neighboring teeth T1 and T2, while sheet 12 is packed into the empty tooth socket E contacting gingival tissue G and extending to bone B (FIG. 4B). Bite block 52 holds sheet 12 in place and covers the socket, thereby helping prevent bleeding at the extraction site and keeping material 12 in place. Device 50 may be dimensioned for treating one extraction site, or multiple adjoining sites as may be needed.

Device 50 is typically applied for several hours following a tooth extraction, and is removed carefully so as not to disturb the clot that normally forms in the extraction socket E. Use of device 50 has been found to prevent "dry socket" and also to promote more rapid healing accompanied by reduction in post-operative pain and swelling. Use of a dressing made of sheet 12 for a few hours per day, for the following two days or thereabouts, prevents infection and maintains the anti-inflammatory effects produced by device 50.

Another treatment device 60, shown in FIGS. 5A and 5B, includes a dental appliance 24 with a pair of disks 62a, 62b connected by at least one tether 64. Tether 64 is made of monofilament nylon, dental floss material, or other suitable material. Tether 64 (and above-described tether 20) may be slightly elastic to help retain device 60 (and device 10) in position. At least one of disks 62a, 62b has a liner 34 made of sheet 12 attached thereto. Device 60 is placed with disks 62 on either side of the affected tooth and gum, so that liner (or liners) 34 contact the area to be treated. Tether 64 maintains device 60 in position during treatment. Like above-described devices 40 and 50, device 60 may be dimensioned for treating one tooth, or a plurality of teeth as may be needed for any particular application.

Figure 6A:
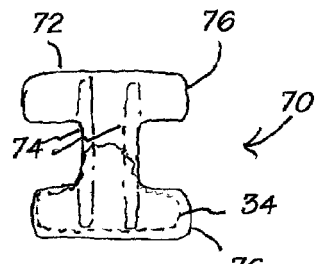
FIGS. 6A–C show another treatment device.

A treatment device according to the present invention may include a shapeable dental appliance that can be customized to fit around and over one or more of the patient's teeth. Such a device 70 is shown in plan view in FIG. 6A, where a moldable plastic pad 72 includes rails 74 (made of wire or other shape-holding material) and wings 76. At least one antimicrobial liner 34 is attached to pad 72, generally as shown. For some applications, rails 70 may be made of the type of alloy known in the art as a "superelastic alloy" or "shape memory alloy" that, when deformed, tends to recover to a preformed shape under the appropriate conditions. Alternatively, pad 72 is a somewhat malleable (i.e., shapeable) material that can readily be conformed so as to engage the treatment site.

Figure 6B:
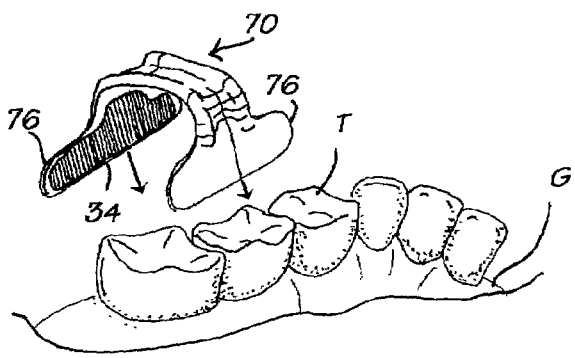
Figure 6C:
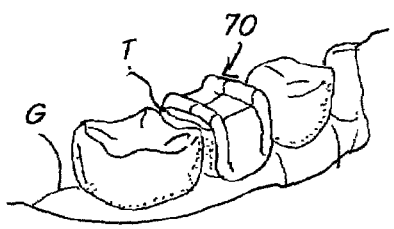

Device 70 is positioned over the tooth T to be treated, and pad 72 is gently pressed into contact with the tooth and adjacent gum tissue (FIGS. 6B and 6C). Excess material may be trimmed from wings 76 if desired. Device 70 may be made in other shapes and sizes, as may be needed for different points of application in the human (or animal) mouth.

Figure 7A:
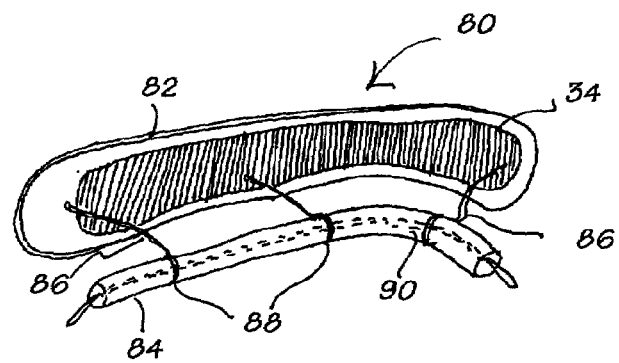
FIGS. 7A and 7B show a device according to the present invention, wherein said device is configured for treating a plurality of teeth.

A periodontal treatment device according to the present invention may be configured for treating several teeth, up to and including all teeth in the patient's upper or lower jaw as may be seen in the following Figures. For example, device 70 can readily be sized for treating a plurality of adjacent teeth. Another device 80 for treating a plurality of adjacent teeth (shown in FIGS. 7A and 7B) includes a dental appliance with a pad or plate 82, a retainer 84 of soft rubber or plastic, and a plurality of tethers 86 (rubber bands of the type commonly used for dental braces, monofilament nylon, dental floss material, or other suitable material). Tethers 86 lie in grooves 88 that prevent slippage. A liner 34 of sheet 12 is attached to an inner side of plate 82.

Figure 7B:
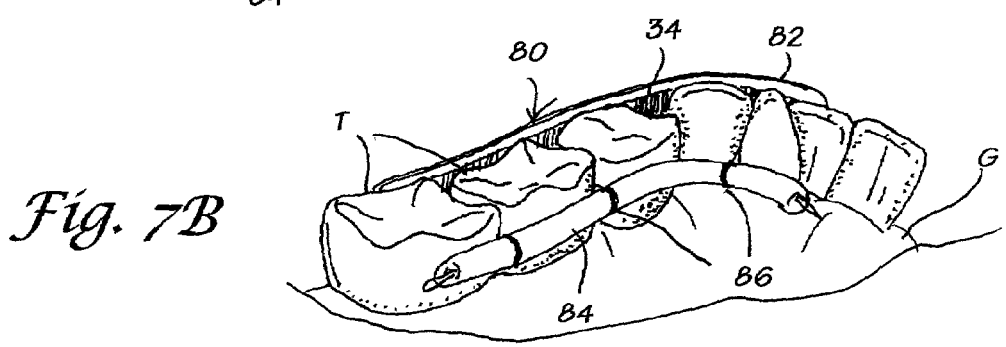

Device 80 is positioned with liner 34 engaging the tooth and gum surfaces to be treated (FIG. 7B). Plate 82 and retainer 84 are held snugly against the opposing tooth and gum surfaces by tethers 86.

Plate 82 is made of a somewhat flexible or moldable (i.e., malleable, shapeable) material that can be shaped to approximately conform to the surface contours of the teeth and gums to be treated. Retainer 84 may have a moldable wire insert 90 (shown in FIG. 7A) that can be shaped to conform to the surfaces of the opposing teeth so as to hold device 80 in place during treatment.

Figure 8A:
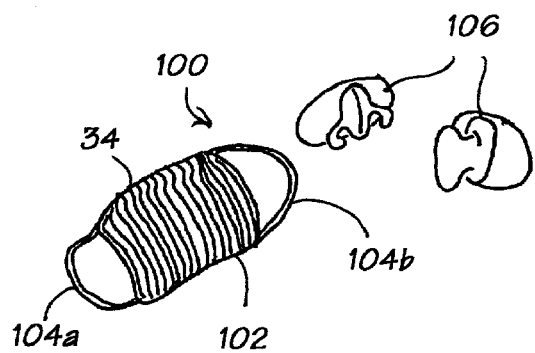
FIGS. 8A–10C show additional devices for treating a plurality of teeth.
Figure 8B:
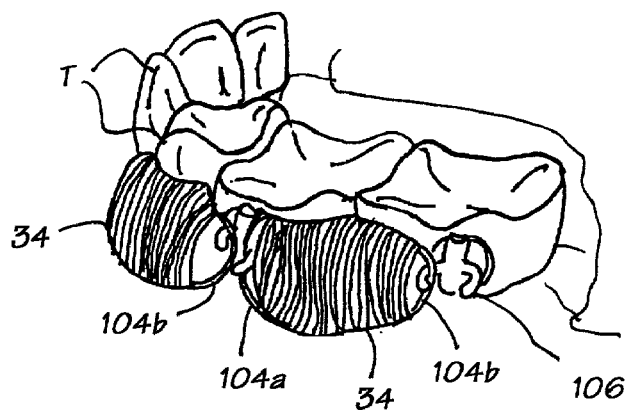

A device 100 having a portion 102 with liner 34 and a pair of rubber bands 104a, 104b is shown in FIG. 8A. Portion 102 is secured to brackets 106, which are the type of brackets commonly used with orthodontic appliances. In use, the appropriate number of brackets 106 are cemented to the patient's teeth (FIG. 8B), and a portion or portions 102 are attached to the brackets via bands 104a, 104b. In this embodiment of the invention, portions 102 are easily removable and may be replaced whenever needed. Portions 102 may be worn for a few hours at a time or continuously, as may be prescribed for each patient.

Figure 9A:
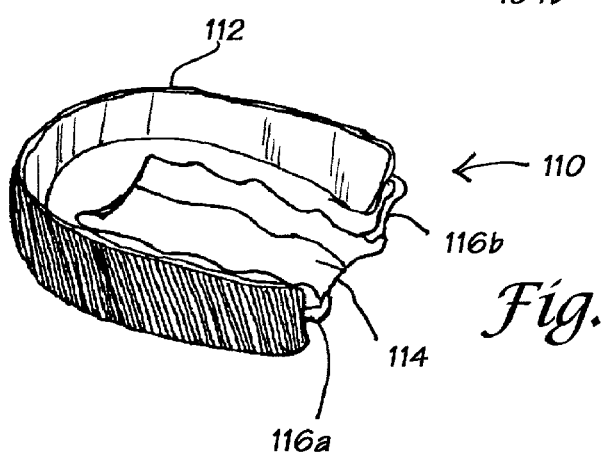
Figure 9B:
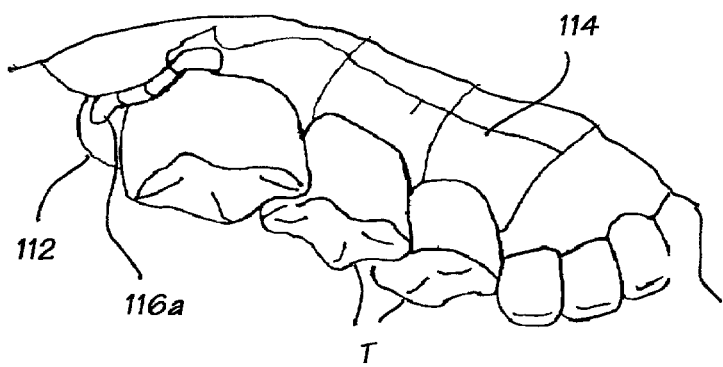

Devices 110 and 120 for treating the entire upper and lower jaws, respectively, are shown in FIGS. 9A–10B. Device 110 includes a portion 112 of above-described sheet 12, and a moldable retainer 114 attached to portion 112 with retainer wires 116a, 116b (FIG. 9A). Portion 112 stretches about teeth T, and is held in place by retainer 114, which is molded to conform to the roof the patient's mouth (FIG. 9B).

Figure 9C:
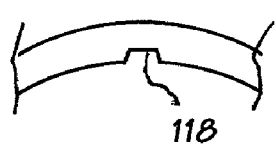

For any devices used for treating the front teeth, a small central notch 118 may be cut in the device as shown in FIG. 9C. A notch accommodates the frenum (a small web of connective tissue that extends between the gum and the lip) that may otherwise, in some patients, interfere with the proper placement of the device. For example, portion 112 could have a notch positioned approximately at its center, as could plate 82 of device 80.

Figure 10A:
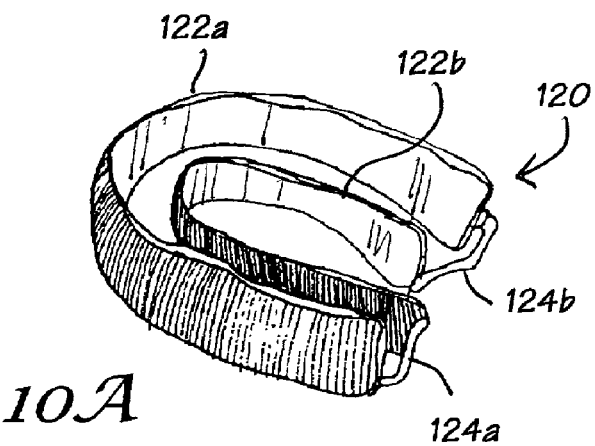
Figure 10B:
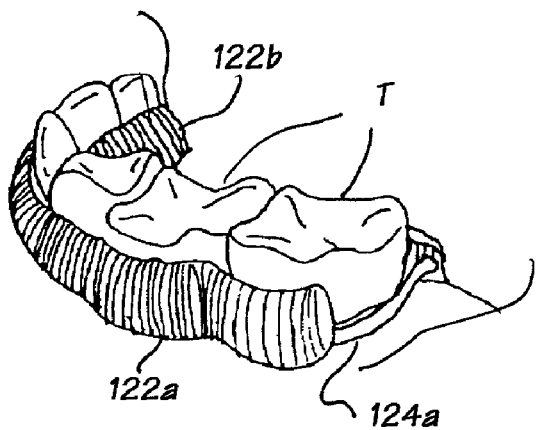
Figure 10C:
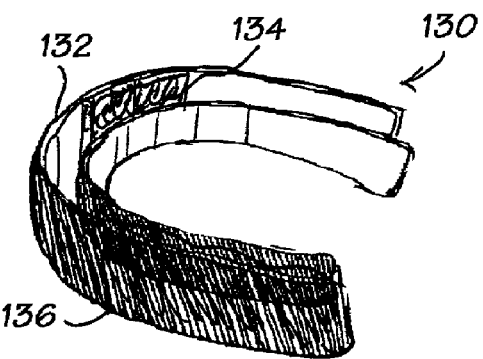
Figure 11:
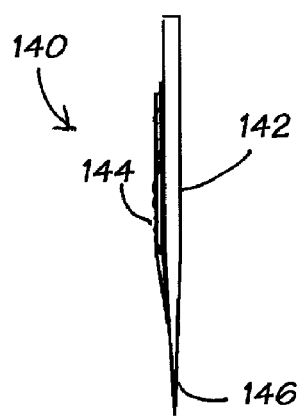
FIG. 11 shows a device for insertion into a gum pocket.

Lower jaw device 120 has one or two portions such as 122a, 122b of sheet 12 connected by retainer wires 124a, 124b (FIG. 10A). Additional retainer wires may be positioned at intervals between 124a, 124b if desired. When installed for use, portions 122a, 122b conform to the inside and outside surfaces of teeth T, held in place by wires 124a, 124b.

Still another device 130 includes an upper or lower bite plate 132 which retains a portion 134 of sheet 12 in the desired position for treatment. Bite plate 132 may be molded in situ over portion 134, thereby helping ensure a good fit. For use during the patient's waking hours, parts of the walls of bite plate 132 could be cut away.

A periodontal treatment device 140 includes a perio-chip 142 with a portion 144 of sheet 12 attached on one side and a tapered end 146 (alternatively, portion 144 can be formed into a sheath about perio-chip 142). Perio-chip 142 is configured for insertion into the perio pocket so that at least some of portion 144 is inside the pocket. Perio-chip 142 is made of a fairly rigid material such as nylon or other plastic.

In all of the above-described embodiments of the invention, sheet 12 may have three layers 14, 16, 18 or consist of just layers 14 and 18. Sheets 12 with a layer 16 are deemed useful for applications where the additional structural support provided by layer 16 may be needed. Sheet 12 may be permanently attached to its respective device, or be replaceable by the user (or caregiver) as may be needed. Depending on the application, devices according to the invention may have one sheet 12 or a plurality of sheets.

Sheet 12 may be provided in virtually any size, thickness, and configuration, including both flat and shaped sheets, as may be convenient for any particular application. Silver-containing material 18 may be loop knit, warp knit, pile, tricot, or some other type of fabric, preferably with a substrate of nylon or other biocompatible material. Polymer layer 14 is at least somewhat resilient or springy, and provides a modicum of shock-absorbing or shock-dampening that adds to patient comfort.

Portions of the dental appliances used with the present invention may be made of dental grade thermoplastic materials that soften when heated and return to their original condition when cooled to room temperature. Such materials include polyvinyl chloride, nylon, fluorocarbon compounds, polyethylene, polyurethane, polystyrene, polypropylene, and various cellulosic and acrylic resins. For example, brace 32 of device 30, sections 42, 44 of device 40, pad 72 of device 70, and plate 82 of device 80 may be wholly or partly made of such materials.

In yet another embodiment of the present invention, layer 16 of sheet 12 may be replaced with (or coated with) an outer layer of a compressible, formable material that can be shaped to any needed form and that retains that form. Suitable materials include the types of dental waxes and dental plastics used in orthodontic devices. A sheet 12 with this type of coating can be cut to any size and shape needed for the above-described devices, which could then be manufactured without plates 42, 44, 62a, 62b, 72, 82, and like structures. Sheet 12 alone would then be shaped to conform to the particular treatment area.

As will now be evident, treatment devices according to the present invention can be manufactured in a variety of useful shapes for use in different sites. The devices are inert until the silver of layer 18 is wetted by any of a variety of agents: water, wound exudate, saliva, or other suitable liquid. Then, at least some free silver ions are released from layer 18 and migrate from layer 18 into the surrounding region. When placed in the patient's mouth so that layer 18 contacts the area to be treated, the saliva may be sufficient to activate this process. Alternatively, composition 10 may be pre-moistened with a suitable liquid.

Sheet 12 (and dental treatment devices made therewith) is self-sterilizing, that is, layer 18 sterilizes itself when wetted as a result of the antimicrobial effect of the silver contained in the layer. As a result, even though the above-described devices are preferably used only once, they may be kept in position for longer periods, or be rinsed and reused, under emergency conditions. Preferably, however, liners 34 are removable and replaceable, so that the patient uses a fresh liner for each scheduled treatment.

A periodontal treatment device according to the present invention provides therapeutic and/or prophylactic activity, including anti-inflammatory and anti-allogenic effects. Importantly, while the device has significant bactericidal, anti-inflammatory, and anti-allogenic effects in the treated area, there are no systemic effects and no entry of silver ions into the circulatory system. The optimum content of silver (or other useful metal or compound) in layer 18 depends on the particular application; thus, compositions with silver contents outside the above-quoted ranges may also be useful for the practice of the invention.

The optimum dimensions and configurations of the device depend on the size and location of the area to be treated, and include considerations of maintaining the position of the device to ensure direct contact between silver-containing layer 18 and the gingival tissues being treated. The device may be custom-made for each individual patient, or provided in a range of standard sizes to fit most individuals. Layer 18 is not known to cause allergic reactions, thus, its use with the invention prevents some of the potentially-harmful side effects associated with other silver delivery systems (such as topical preparations containing silver sulfadiazine, silver thiosulfate, and other silver compounds). Sheet 12 is nonhazardous, conformable to the shape of the site to be treated, readily adaptable to diverse clinical situations, and safe and easy to use.

With respect to the above description of the invention, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing description is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention. Thus, it will be apparent to those skilled in the art that many changes and substitutions can be made to the preferred embodiment herein described without departing from the spirit and scope of the present invention as defined by the appended claims.

What is claimed is:

1. A treatment device, comprising:
   an antimicrobial sheet material having
      a first layer of a gel composition including a block copolymer and mineral oil, and
      a second layer engaging at least one side of said first layer, said second layer containing a bactericidal metal; and
   means for retaining said antimicrobial sheet material in a selected position in a body cavity of a user.

2. The device is recited in claim 1, wherein at least a portion of said bactericidal metal is silver.

3. The device as recited in claim 1, wherein at least a portion of said bactericidal metal is crystalline silver.

4. The device as recited in claim 1, wherein said bactericidal metal further comprises silver, said silver mechanically attached to said second layer so that, when said layer is wetted, at least a portion of said silver is released in the form of ionic silver.

5. The device as recited in claim 1, wherein said second layer further comprises silver-containing nylon fabric.

6. The device as recited in claim 1, wherein said second layer is selected from the group consisting of (a) a coating on said first layer, said coating containing said bactericidal metal, (b) a quantity of said bactericidal metal in said first layer, and (c) a silver-containing material attached to said first layer.

7. The device as recited in claim 1, wherein said antimicrobial sheet material further comprises at least one third layer engaging another side of said first layer, said at least one third layer made of moisture-absorbing material, moisture-permeable material, or moisture-impermeable material, or gas-permeable material.

8. The device as recited in claim 1, wherein said retaining means further comprises a dental appliance.

9. The device as recited in claim 1, wherein said retaining means further comprises a tether.

10. The device as recited in claim 1, wherein said retaining means further comprises an appliance made of a somewhat flexible, conformable material.

11. The device as recited in claim 1, wherein said retaining means further comprises a shapeable appliance.

* * * * *